(12) United States Patent
Burg et al.

(10) Patent No.: US 7,659,373 B2
(45) Date of Patent: Feb. 9, 2010

(54) ERYTHROPOIETIN WITH HIGH SPECIFIC ACTIVITY

(75) Inventors: Josef Burg, Weilheim (DE); Karl-Heinz Sellinger, Weilheim (DE); Anton Haselbeck, Weilheim (DE); Hans Koll, Weilheim (DE)

(73) Assignee: Roche Diagnostics GmbH, Mannheim (DE)

( * ) Notice: Subject to any disclaimer, the term of this patent is extended or adjusted under 35 U.S.C. 154(b) by 191 days.

(21) Appl. No.: 11/201,006

(22) Filed: Aug. 9, 2005

(65) Prior Publication Data
US 2005/0288220 A1  Dec. 29, 2005

Related U.S. Application Data

(62) Division of application No. 09/555,950, filed as application No. PCT/EP98/07876 on Dec. 3, 1998, now abandoned.

(30) Foreign Application Priority Data

| Dec. 3, 1997 | (DE) | ................................. 197 53 681 |
| Jul. 17, 1998 | (EP) | ................................. 98113415 |

(51) Int. Cl.
| A61K 35/14 | (2006.01) |
| A61K 38/00 | (2006.01) |
| A61K 51/00 | (2006.01) |
| A01K 38/16 | (2006.01) |
| C07K 14/00 | (2006.01) |
| C07K 17/00 | (2006.01) |
| C07K 1/00 | (2006.01) |

(52) U.S. Cl. ....................... 530/380; 530/350; 530/395; 514/2; 424/1.69

(58) Field of Classification Search .................. 530/395
See application file for complete search history.

(56) References Cited

U.S. PATENT DOCUMENTS

| 4,745,099 A | * | 5/1988 | Akamatsu et al. ............... 514/8 |
| 4,835,260 A | * | 5/1989 | Shoemaker .................. 530/397 |
| 5,106,954 A | * | 4/1992 | Fibi et al. .................... 530/324 |
| 5,459,031 A | * | 10/1995 | Blumen et al. .................. 435/3 |
| 5,641,670 A | * | 6/1997 | Treco et al. .................. 435/325 |
| 5,789,390 A | * | 8/1998 | Descamps et al. ............. 514/44 |
| 5,856,298 A | * | 1/1999 | Strickland ....................... 514/8 |

FOREIGN PATENT DOCUMENTS

| WO | WO-93/09222 | 5/1993 |
| WO | WO-94/12650 | 6/1994 |
| WO | WO-95/31560 | 11/1995 |
| WO | WO-96/35718 | 11/1996 |
| WO | WO-99/05268 | 2/1999 |

OTHER PUBLICATIONS

Watson et al. Structure determination of the intact major sialylated oligosaccharide chains of recombinant human erythropoietin expressed in Chinese hamster ovary cells. Glycobiology. 1994, 4(2): 227-237.*
Takeuchi et al. Relationship between sugar chain structure and biological activity of recombinant human erythropoietin produced in Chinese hamster ovary cell. Proc. Natl. Acad. Sci. Oct. 1989, 86: 7810-7822.*
Takeuchi et al. #2. Structures and functional roles of the sugar chains of human erythropoietins. Glycobiology. Sep. 1991;1(4):337-46. Review.*
Descamps et al. Keratinocytes as a target for gene therapy. Sustained production of erythropoietin in mice by human keratinocytes transduced with an adenoassociated virus vector. Arch Dermatol. Oct. 1996;132(10):1207-11 (abstract).*
Ohashi, et al., "Purification and Characterization of Recombinant Human Erythropoietin Expressed in Human Cervix Carcinoma HeLa Cells," Trends in Animal Cell Culture Technology (1990) 115-120.
Bioindustry, vol. 8, No. 4 (1991), p. 21-31.
Summary Japan Fermentation Technology Associated 1991 Meeting, 1991, p. 30.

* cited by examiner

*Primary Examiner*—Maury Audet
(74) *Attorney, Agent, or Firm*—Fulbright & Jaworski LLP

(57) ABSTRACT

The invention concerns new EPO compositions with high specific activity which are characterized by a high proportion of N-acetyl-lactosamine units or/and tetraantennary branches in the carbohydrate structure. In addition the invention concerns a process for producing such EPO products.

36 Claims, 3 Drawing Sheets

Figure 1:
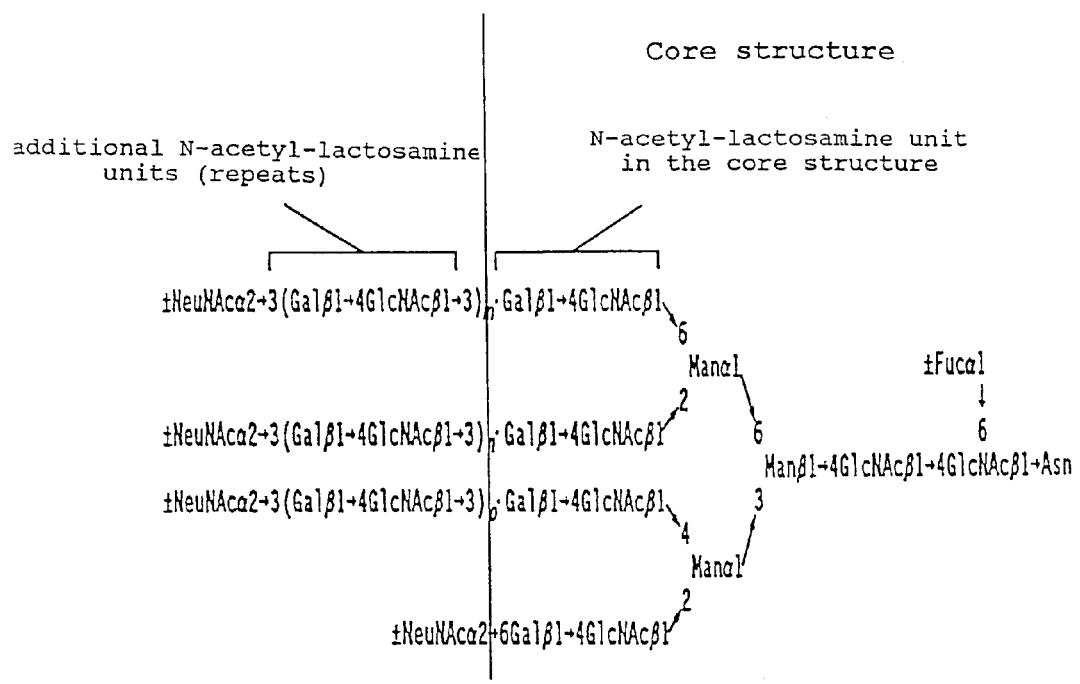

Figure 1: Tetraantennary N-linked carbohydrate structure with additional N-acetyl-lactosamine units (repeats) and sialic acids

ERYTHROPOIETIN WITH HIGH SPECIFIC ACTIVITY

RELATED APPLICATIONS

This application is a divisional application of application Ser. No. 09/555,950 filed Aug. 17, 2000, now abandoned which claims priority of PCT/EP98/07876 filed Dec. 3, 1998 and German Patent Application No. 197 53 681.6 filed Dec. 3, 1997 and European Patent Application No. 98113415.8 filed Jul. 17, 1998, all incorporated herein in their entireties.

DESCRIPTION

The invention concerns new EPO compositions with high specific activity which are characterized by a high content of N-acetyl-lactosamine units or/and tetraantennary branches in the carbohydrate structure. The invention also concerns a process for isolating such EPO products.

Erythropoietin (EPO) is a human glycoprotein which stimulates the production of red blood cells. EPO only occurs in the blood plasma of healthy persons in very low concentrations so that it is not possible to provide larger amounts in this manner. EP-B1-0 148 605 and EP-B1-0 205 564 describe the production of recombinant human EPO in CHO cells. The EPO described in EP-B1-0 148 605 has a higher molecular weight than urinary EPO and no O-glycosylation. The EPO described in EP-B1-0 205 564 from CHO cells is now available in large amounts and in a pure form.

Furthermore the isolation of human EPO from the urine of patients with aplastic anaemia is known (Miyake et al., J. Biol. Chem. 252 (1977), 5558-5564).

Recombinant and urinary EPO are isolated as a mixture of various isoforms which are known to differ in their degree of sialylation. These EPO isoforms have different isoelectric points and can be separated by isoelectric focussing or capillary electrophoresis (see Tsao et al., Biotech. Bioeng. 40 (1992), 1190-1196; Nieto et al., Anal. Commun. 33 (1996), 425-427; Tran et al., J. Chromatogr. 542 (1991), 459-471; Bietot et al., J. Chromatogr. 759 (1997), 177-184; Watson et al., Anal. Biochem. 210 (1993), 389-393). The isoforms with the highest number of sialic acids have the highest specific activity, whereas those with the lowest number have the lowest activity (see e.g. Imai et al., Eur. J. Biochem. 194 (1990), 457-462; EP-A-0 428 267).

Takeuchi et al., (Proc. Natl. Acad. Sci. USA 86 (1989), 7819-7822) describe a relationship between the biological activity and the sialic acid content and the ratio of biantennary and tetraantennary carbohydrate structures. Takeuchi et al., additionally conclude that the N-acetyl-lactosamine units present in the EPO carbohydrate structure do not correlate with the biological activity.

Fukuda et al., (Blood 73 (1989), 84-89) deal with the rate of elimination of EPO from the blood circulation which makes an important contribution to the biological activity and conclude that EPO with a relatively large number of N-acetyl-lactosamine units is more rapidly removed from the circulation than EPO without lactosamine units. Morimoto et al., (Glycoconjugate J. 13 (1996), 1053-1120) describe the separation of EPO isoforms by means of mono-Q chromatography so that the individual fractions are then only composed of a few isoforms. The investigations carried out on these fractions show an equidistribution of all structures in all fractions. No correlation was found between the content of biantennary or tetraantennary structures or the content of N-acetyl-lactosamine units and the specific activity.

Thus the said prior art shows that there is a general correlation of the biological activity with the sugar structure especially with regard to the content of sialic acids. However, there is no indication at all that the content of tetraantennary structures or/and the content of N-acetyl-lactosamine correlates directly with the biological activity.

When purifying EPO preparations it was surprisingly found that an increase of the content of tetraantennary carbohydrate structures or/and N-acetyl-lactosamine units in the carbohydrate structure leads to a significant improvement of the specific biological activity. This is particularly applicable when EPO is produced in a human cell line according to the European Application 97 112 640.4.

Comparative activity investigations of individual EPO preparations or EPO isoforms whose carbohydrate structure essentially only differs in the content of N-acetyl-lactosamine units (LE units) show a significantly higher activity for the preparations or isoforms with the higher content of N-acetyl-lactosamine units for the same sialic acid content and for about the same degree of antennarity. In this connection antennarity is understood as the relative, average content (in %) of biantennary, triantennary and tetraantennary N-linked carbohydrate chains of the EPO preparations or of the isolated EPO isoforms relative to the total number of N-linked carbohydrate chains. Furthermore it was found that especially in preparations or isoforms with an elevated content of tetraantennary structures, the total content of lactosamine units is extremely important for the in vivo activity. An increase in the total content of N-acetyl-lactosamine units, e.g. in the form of additional extensions of the core structure with LE units (so-called repeats), can considerably increase the biological activity. It was additionally found that an increase in the content of tetraantennary structures can improve the biological activity.

Consequently, if one intends to produce an EPO preparation with the highest possible specific activity and in a high yield, then the purification steps, the production cells or/and the culture thereof must be selected and optimized to achieve the highest possible content of tetraantennary carbohydrate structures or/and the highest possible content of N-acetyl-lactosamine units.

A first aspect of the present invention concerns an EPO composition which is composed essentially of glycosylated EPO molecules which contain a proportion of at least 75%, preferably of at least 80%, particularly preferably of at least 85% and most preferably of at least 90% of tetraantennary structures relative to the total number of carbohydrate chains i.e. the sum of biantennary, triantennary and tetraantennary structures.

A further aspect of the invention concerns an EPO composition which is essentially composed of glycosylated EPO molecules which contain an average number of at least 3.7, preferably of at least 4.0, particularly preferably of at least 4.3 and most preferably at least 4.5 N-acetyl-lactosamine units with reference to the average composition per N-linked carbohydrate chain of the EPO molecule or a number of at least 11.1, preferably of at least 12.0, particularly preferably of at least 13.0 and most preferably of at least 13.5 N-acetyl-lactosamine units with reference to all three N-linked carbohydrate structures (total N-glycosylation) of the EPO molecule.

A further aspect of the invention concerns an EPO composition which is essentially composed of glycosylated EPO molecules which have a value for the product of the average total number of N-acetyl-lactosamine units per EPO molecule multiplied by the average sialic acid content per molecule of EPO of at least 130, preferably of at least 135, particularly preferably of at least 140 and most preferably of at least 160.

In this connection the term "essentially" means that the desired EPO molecules are present in a proportion of preferably at least 80%, particularly preferably at least 90% and most preferably of at least 95% relative to the total number of EPO molecules in the composition.

Yet a further aspect of the invention concerns an EPO composition which is composed of glycosylated EPO molecules which have an average proportion of at least 75%, preferably of at least 80% and particularly preferably of at least 85% tetraantennary structures relative to the total number of carbohydrate chains.

In addition the invention concerns an EPO composition which is composed of glycosylated EPO molecules which have an average number of at least 3.7, preferably of at least 4.0 and particularly preferably of at least 4.3 and most preferably of at least 4.5 N-acetyl-lactosamine units with reference to the average composition per N-linked carbohydrate chain of the EPO molecule or contain a number of at least 11.1, preferably at least 12.0, particularly preferably of at least 13.0 and most preferably of at least 13.5 N-acetyl-lactosamine units with reference to all 3 N-linked carbohydrate structures of the EPO molecule.

The maximum proportion of tetraantennary structures can reach up to 100% of the total carbohydrate chains where each tetraantennary structure contains 4 N-acetyl-lactosamine units in the core structure of the N-linked sugar. Additional N-acetyl-lactosamine units which occur as extensions of the core structure as so-called repeats can increase the number of N-acetyl-lactosamine units per carbohydrate structure as well as in the total glycosylation. The number of N-acetyl-lactosamine units per glycosylation site (i.e. per N-linked carbohydrate structure) can thus be up to 6 (tetraantennary structure and 2 additional N-acetyl-lactosamine units in the form of repeats) (cf. FIG. 1) or can—in the case of structures with more than 2 additional N-acetyl-lactosamine units—be even higher. The number of N-acetyl-lactosamine units can be up to 18 or higher with reference to the total glycosylation (three N-linked carbohydrate structures).

Yet a further aspect of the invention concerns an EPO composition which is composed of glycosylated molecules which has an average value for the product of the average total number of N-acetyl-lactosamine units of the EPO molecule multiplied by the average sialic acid content per molecule of EPO of at least 130, preferably of at least 135, particularly preferably of at least 140 and most preferably of at least 160.

A further subject matter of the invention is an EPO composition which has the features of at least two or several of the previously mentioned aspects.

The composition according to the invention can be composed of one or several isoforms i.e. EPO molecules with different isoelectric points in the isoelectric focussing. The composition according to the invention preferably comprises a mixture of at least 2, e.g. of 2 to 5 isoforms, in particular a mixture of 3 or 4 isoforms.

The specific activity of the composition according to the invention is preferably at least 175,000 IU/mg, in particular 200,000 IU/mg in vivo (normocythaemic mouse). The specific activity is particularly preferably in the range of about 200,000 to 400,000 IU/mg or 450,000 IU/mg protein, most preferably in the range of 250,000 to 400,000 IU/mg or 450,000 IU/mg protein.

In the composition according to the invention the average sialic acid content or the average number of sialic acid residues per molecule EPO is preferably 11 to 14, particularly preferably at least 11.5 and most preferably at least 12.5.

The EPO composition according to the invention can, on the one hand, be obtained from EPO molecules which are the product of an expression of exogenous DNA in mammalian cells e.g. in rodent cells such as CHO or BHK cells as described in EP-B-0 205 564. Alternatively the composition can also be composed of EPO molecules which are the product of an expression of endogenous DNA after gene activation in human cells e.g. in immortalized cell lines such as Namalwa (Nadkarni et al., Cancer 23 (1969), 64-79), HT1080 (Rasheed et al., Cancer 33 (1973), 1027-1033) or HeLa S3 (Puck et al., J. Exp. Meth. 103 (1956), 273-284). Such processes are described in the European Patent Application 97 112 640.4 the disclosure of which is made part of the present application.

Further important parameters for the biological activity of EPO are the proportion of carbohydrate chains with repeats i.e. additional N-acetyl-lactosamine units relative to the total number of N-linked carbohydrate chains as well as the value of the product of this proportion of repeats and the proportion of tetraantennary carbohydrate chains relative to the total number of carbohydrate chains. In the case of EPO from CHO cells the proportion of repeats is preferably at least 30%, particularly preferably at least 35% and most preferably at least 40%. In the case of EPO from human cells such as HeLa cells the proportion of repeats is preferably at least 10%, particularly preferably at least 12% and most preferably at least 14%. Accordingly, in the case of EPO from CHO cells the value for the product of the proportion of carbohydrate chains with N-acetyl-lactosamine repeats relative to the total number of carbohydrate chains and the proportion of tetraantennary structures relative to the total number of carbohydrate chains is preferably at least 2400, particularly preferably at least 2800 and most preferably at least 3400. In the case of EPO from human cells the value is preferably at least 800, particularly preferably at least 960 and most preferably at least 1100.

An EPO composition is preferably used which has been produced by culturing EPO production cells in a culture medium containing a low content of serum e.g. a maximum of 1% (v/v) or especially in a serum-free culture medium (cf. for this WO 96/35718). Examples of suitable culture media are RPMI 1640 or DMEM.

The EPO composition according to the invention can be formulated as a pharmaceutical preparation optionally together with common pharmaceutical diluents, auxiliary substances and carriers. The EPO composition according to the invention that can be used to produce a pharmaceutical preparation has a purity of preferably at least 99% and particularly preferably of at least 99.9% as determined by reverse phase HPLC (e.g. on a Vydac C4 column) or/and size exclusion chromatography (e.g. on a TSK 2000SW Ultrapac column).

In addition the composition according to the invention has a DNA content of preferably <10 pg. particularly preferably <5 pg and most preferably <1 pg DNA per 10,000 IU protein. Furthermore the composition according to the invention is preferably substantially free of bacterial impurities (<1 CFU/ml) and endotoxins (<1 EU/10,000 IU protein).

The DNA content can be determined by a hybridization test using radioactively or fluorescent-labelled DNA. Commercially available purified human DNA is for example used as the probe DNA. The human DNA can additionally be used as a standard for the test. The lower limit of detection of such a hybridization test is about 0.3 pg/10,000 IU EPO. The germ and endotoxin content of the EPO preparation can be determined by standardized methods as described in Pharm. Eu. or USP.

An EPO composition which preferably has the features desired by the invention is obtainable by at least one of the following measures:
(a) selection of a suitable production cell line which is able to produce carbohydrate chains with a high proportion of tetraantennary structures or/and N-acetyl-lactosamine units,
(b) selection of suitable culture conditions for the cell culture in order to produce carbohydrate chains with a high proportion of tetraantennary structure or/and N-acetyl-lactosamine units and
(c) separation of undesired components from a known composition of EPO molecules while enriching EPO molecules which contain carbohydrate chains with a high proportion of tetraantennary structures or/and N-acetyl-lactosamine units.

Measure (a) comprises the selection of a suitable production cell. In this case one can, on the one hand, use cells which are known to have a tendency to produce the desired carbohydrate chain structures in a high yield. Examples of such cell lines are cells derived from the hamster such as CHO or BHK and human cell lines such as HeLa, Namalwa, HT1080 or cell lines derived therefrom. Hela S3 cells or modified CHO cells are particularly preferred.

On the other hand, it is also possible to specifically produce suitable production cells by overexpressing certain glycosylation enzymes in the cell e.g. by recombinant expression or/and by endogenous gene activation. Examples of such glycosylation enzymes are sialyl transferases, N-acetyl-glucosaminyl transferases and galactosyl transferases.

Measure (b) comprises the selection of suitable culture conditions in the cell culture. In a first embodiment of the invention measure (b) comprises adding a mixture of at least two and preferably at least three carbohydrates to the culture medium. The carbohydrates are preferably selected from monosaccharides and disaccharides such as glucose, glucosamine, ribose, fructose, galactose, mannose, sucrose, lactose, mannose-1-phosphate, mannose-1-sulfate and mannose-6-sulfate. Nutrient media are for example suitable which contain glucose or/and mannose or/and galactose. Particularly good results were obtained with nutrient media which contain a mixture of glucose, galactose and mannose for example in a mass ratio of 1:(0.5-3):(1-5) and in particular of 1:(0.7-2.4):(1.8-4.0) where each of the carbohydrates is particularly preferably used in the D(+) form. The total concentration of all sugars during the fermentation is preferably in a range of 0.1 to 10 g/l, particularly preferably in a range of 2 to 6 g/l in the culture medium. The carbohydrate mixture is preferably added dependent on the respective requirement of the cells as elucidated in more detail in the following.

According to a further preferred embodiment measure (b) comprises the controlled addition of nutrients which is preferably in accordance with requirements comprising at least one essential amino acid for the cultured cell line or/and at least one carbohydrate dependent on the respective cell requirements. In this manner a considerably improved glycosylation is obtained in large fermenters (volume >1 l, e.g. 50-10,000 l) even with a high cell density fermentation (cell density at harvest >10×10$^5$ cells/ml and preferably >20×10$^5$ cells/ml). For this purpose the concentration of parameters which correlate with the nutrient requirements of the cells is determined continuously or at suitable time intervals e.g. at least once daily and their consumption rates are calculated. This enables the nutrient requirements of the cells to be determined quantitatively or/and qualitatively. Such parameters can be nutrients or metabolic products of the cells such as the glutamine, ammonium, glucose or/and lactate concentration and especially the glutamine concentration.

The nutrients added according to this aspect of the invention comprise essential amino acids e.g. glutamine or/and tryptophan or/and carbohydrates and preferably in addition non-essential amino acids, vitamins, trace elements, salts or/and growth factors e.g. insulin. The nutrients particularly preferably include at least one essential amino acid and at least one carbohydrate. These nutrients are preferably metered into the culture medium in a dissolved state. The nutrient solutions preferably contain glutamine and carbohydrates especially admixture of at least two carbohydrates as mentioned above. A mixture of glucose, galactose and mannose is particularly preferably used. In addition it is preferred that the nutrients are added according to needs over the entire growth phase of the cells i.e. dependent on the concentration of the selected parameters measured in the culture medium.

The quantity ratio of glutamine to carbohydrates in the nutrient solution is preferably selected such that it essentially corresponds to the consumption ratio in the fermenter. This enables a substantially constant concentration of the individual substrates to be maintained in the fermenter. The concentration of glutamine is preferably maintained at a value which is <150 mg/l in the culture medium and prevents the development of an ammonium concentration ≧2.3 mmol/l in the culture medium. During the fermentation the total concentration of the sugars is preferably in a range of 0.1 to 10 g/l, particularly preferably in a range of 2 to 6 g/l culture medium as already explained. The nutrient solution that is used contains a mass ratio of glutamine to sugars which is preferably in a range of 1:3 to 20 and particularly preferably of 1:5 to 15 with reference to the total sugar. When a nutrient solution is used which contains glutamine as well as the three sugars glucose, galactose and mannose, the mass ratio of glutamine to the sugars is preferably 1:(1 to 3):(1 to 5):(2 to 8) and particularly preferably 1:(1.5 to 2.2):(1.5 to 3.6):(4 to 6).

The culture is preferably carried out as a repeated batch process in which a portion of the culture broth is harvested after a growth phase and the remainder of the culture broth remains in the fermenter which is subsequently again filled up with fresh medium to the working volume. The process according to the invention enables glycosylated EPO to be harvested in very high yields. Hence the concentration at the time of harvest is for example at least 30 mg and in particular at least 40 mg EPO per 1 culture medium.

Yet a further aspect of the invention is a process for isolating EPO from eukaryotic cells in which the eukaryotic cells are cultured in a suitable medium and the EPO is isolated from the culture supernatant, the process being characterized in that the culture is carried out at a temperature of ≦36° C., preferably between 30 and 35.5° C. and particularly preferably between 33 and 35.0° C. It was surprisingly found that the proportion of EPO with the desired glycosylation can be considerably increased by lowering the temperature during the culture.

Measure (c) comprises the separation of undesired components from a known EPO composition whose carbohydrate structure does not fulfil the specifications of the present application. This can for example be carried out by chromatographic purification of the EPO preparations e.g. by affinity chromatography on triazine dye gels, preferably Cibacron Blue dye gels. Undesired components can also be additionally separated using hydrophobic interaction chromatography and reversed phase HPLC. Ligands that are suitable for this are butyl, pentyl, octyl, octadecyl and phenyl residues.

The reversed phase chromatography step is preferably carried out at a pH value in the range of 6.0 to 8.5 and particularly preferably of 7.0 to 8.0. Suitable eluants are for example acetonitrile, ethanol or isopropanol, preferably acetonitrile.

Suitable fractions can be determined, pooled and finally processed further using capillary zone electrophoretic analysis (CZE). In addition EPO molecules with a high content of N-acetyl-lactosamine units can be directly enriched using lectins from tomatoes or potatoes (Merkle, Cummings, J. Biol. Chem. 262 (1987), 8179-8189). Such lectins are preferably used for example in an immobilized form.

A further subject matter of the invention is a process for increasing the specific activity of an EPO composition wherein EPO molecules are enriched in the composition which have
(a) a high proportion of tetraantennary carbohydrate structures,
(b) a large number of N-acetyl-lactosamine units
(c) a high value for the product of the number of N-acetyl-lactosamine units and the sialic acid content,
(d) a high proportion of N-acetyl-lactosamine repeats or/and
(e) a high value for the product of the proportion of N-acetyl-lactosamine repeats and the proportion of tetraantennary carbohydrate structures.

This enrichment can be achieved by one or several of the above-mentioned measures (a), (b) and (c).

The present invention is further elucidated by the following figures and examples.

Figure 2:
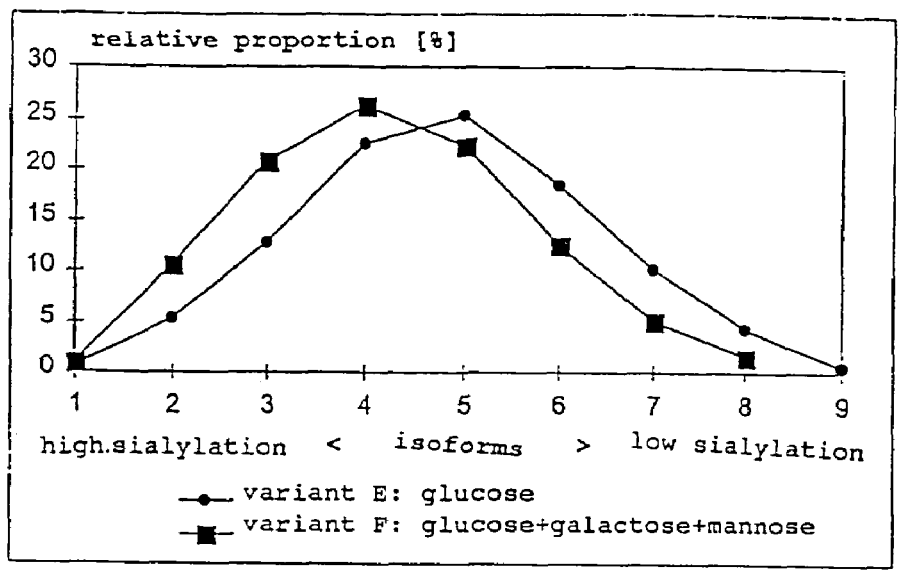
Figure 3:
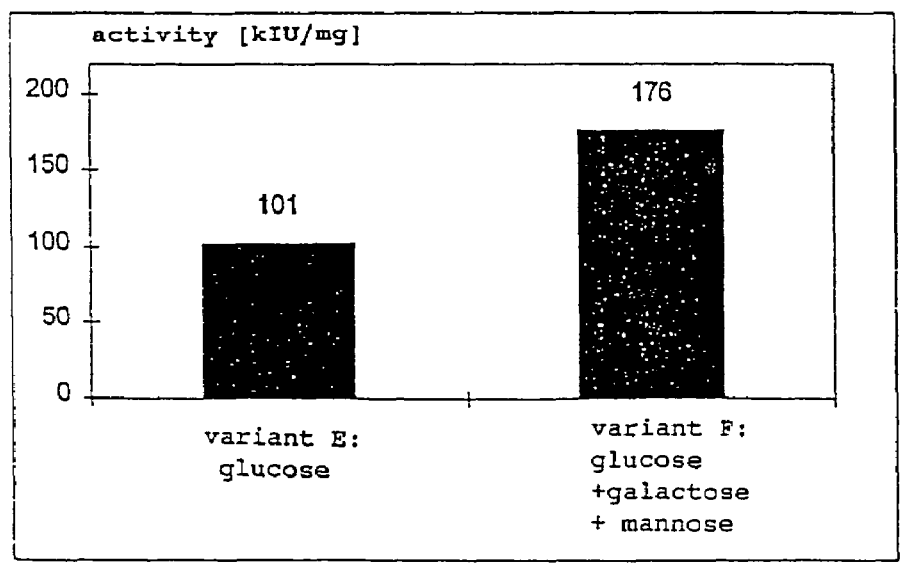
Figure 4:
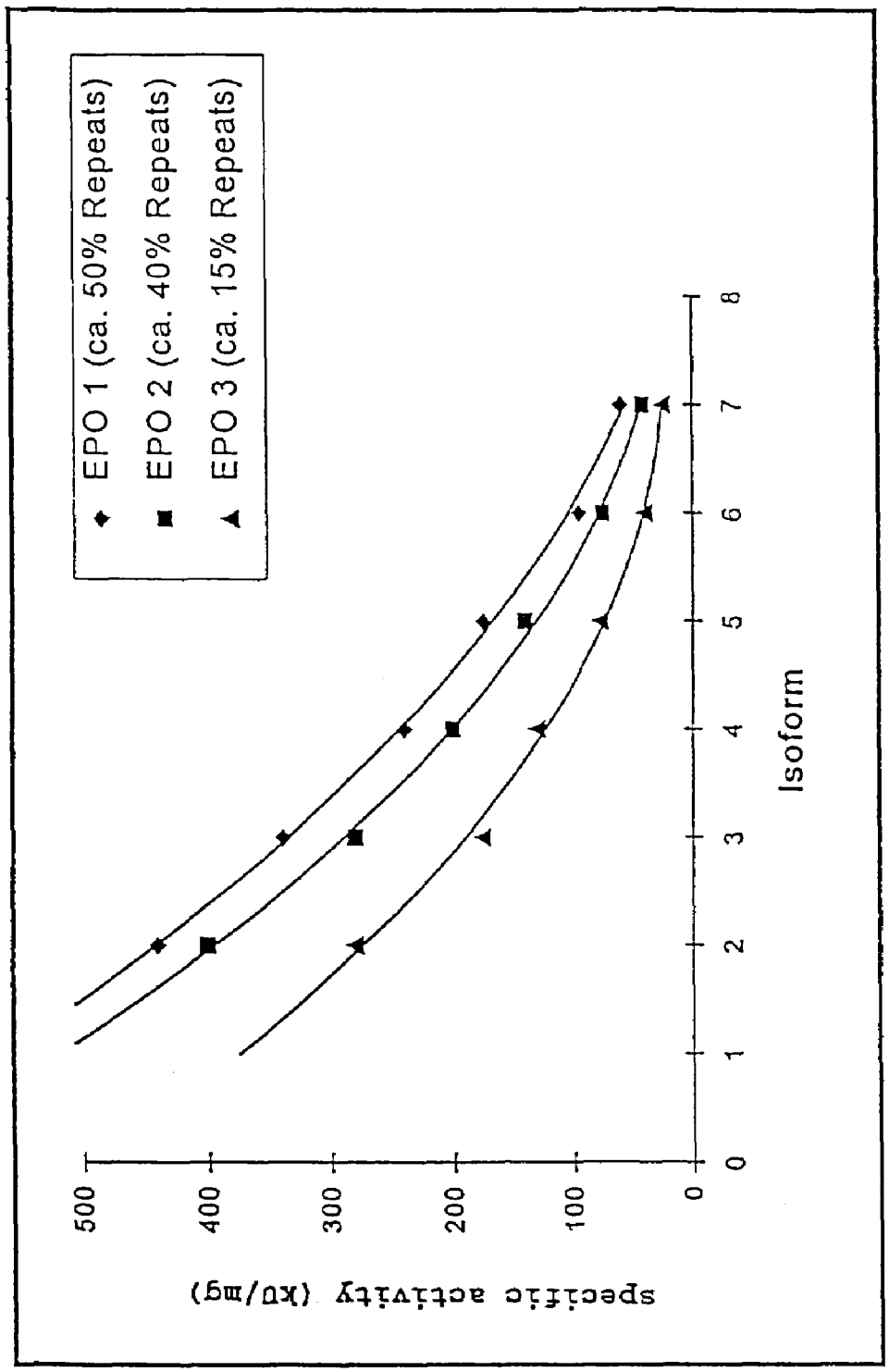

FIG. 1: shows a figure of a tetraantennary carbohydrate structure with additional N-acetyl-lactosamine units (repeats) and sialic acids, FIG. 2: shows the dependence of the relative proportion of individual EPO isoforms on the carbohydrates added to the culture medium, FIG. 3: shows the dependence of the biological activity of EPO preparations on the carbohydrates added to the culture medium, FIG. 4: shows the dependence of the biological activity of EPO isoforms on the number of N-acetyl-lactosamine repeat units.

EXAMPLE 1

Purification of EPO from Culture Supernatants of Cell Lines

Essentially two methods were used to purify EPO from cell culture supernatants of human cells or CHO cells which differ in the number and principle of the chromatographic steps and were used depending on the composition of the medium and the EPO concentration:
Method 1: 1st step: blue-Sepharose column
    2nd step: butyl-Sepharose column
    3rd step: hydroxyapatite column
    4th step: concentration
Method 2: 1st step: blue-Sepharose column
    2nd step: hydroxyapatite column
    3rd step: concentration
    (alternative 3rd step: RP-HPLC)
Example of a purification of a HeLa S3 cell culture supernatant containing 2% (v/v) foetal calf serum (FCS) by method 1:

1. Blue-Sepharose Column:
A 5 ml Hi-Trap Blue column (ready-made blue-Sepharose column from Pharmacia) was equilibrated with at least 5 column volumes (CV) buffer A (20 mM Tris-HCl, pH 7.0; 5 mM $CaCl_2$; 100 mM NaCl). Subsequently 70 ml Hela cell supernatant (containing ca. 245 μg EPO and 70-100 mg total protein) was absorbed overnight at a flow rate of 0.5 ml/min in a recycling procedure.

The column was washed with at least 5 CV buffer B (20 mM Tris-HCl, pH 7.0; 5 mM $CaCl_2$; 250 mM NaCl) and at least 5 CV buffer C (20 mM Tris-HCl, pH 7.0; 0.2 mM $CaCl_2$, 250 mM NaCl) at 0.5 ml/min. The success of the washing was monitored by measuring the protein content at OD 280.

EPO was eluted with buffer D (100 mM Tris-HCl, pH 7.0; 0.2 mM $CaCl_2$; 2 M NaCl) at a flow rate of 0.5 ml/min. The elution solution was collected in 1-2 ml factions.

The EPO content of the fractions, wash solutions and the eluate was determined by reverse phase (RP)-HPLC by applying an aliquot to a POROS R2/H column (Boehringer Mannheim). Alternatively an immunological dot-blot was carried out for the qualitative identification of fractions containing EPO.

Fractions of the elution containing EPO (8-12 ml) were pooled and applied to a butyl-Sepharose column.

The yield after the blue-Sepharose column was ca. 175 μg EPO (corresponds to ca. 70%). In general the yield after blue-Sepharose was between 50 and 75%.

2. Butyl-Sepharose Column (Hydrophobic Interaction Chromatography
A self-made 2-3 ml butyl-Sepharose column (material: Toyopearl butyl S650) was equilibrated with at least 5 CV buffer D (100 mM Tris-HCl, pH 7.0; 0.2 mM $CaCl_2$; 2 M NaCl) and subsequently the blue-Sepharose pool from 1 containing EPO (ca. 150 μg EPO) was absorbed at a flow rate of 0.5 ml/min.

The column was washed with at least 5 CV buffer E (20 mM Tris-HCl, pH 7.0; 2 M NaCl and 10% isopropanol) at 0.5 ml/min. The success of the washing was monitored by measuring the protein content at OD 280.

EPO was eluted with buffer F (20 mM Tris-HCl, pH 7.0; 2 M NaCl and 20% isopropanol) at room temperature and at a flow rate of 0.5 ml/min. The elution solution was collected in 1-2 ml factions.

The EPO content of the fractions, wash solutions and the eluate was determined by RP-HPLC by applying an aliquot to a POROS R2/H column. Alternatively an immunological dot-blot was carried out for the qualitative identification of fractions containing EPO.

Fractions of the elution containing EPO (10-15 ml) were pooled and applied to a hydroxy-apatite column.

The yield of the butyl-Sepharose column was ca. 130 μg EPO (corresponds to ca. 85%). In general the yield of the butyl-Sepharose was between 60 and 85% of the applied blue-Sepharose pool.

3. Hydroxyapatite Column
A 5 ml hydroxyapatite column (ready-made Econo-Pac CHT II from BioRAD) was equilibrated with at least 5 CV buffer F (20 mM Tris-HCl, pH 7.0; 2 M NaCl; 20% isopropanol) and subsequently the butyl-Sepharose pool from 2 containing EPO (ca. 125 μg EPO) was absorbed at a flow rate of 0.5 ml/min.

The column was washed with at least 5 CV buffer G (20 mM Tris-HCl, pH 7.0; 2 M NaCl) at 0.5 ml/min. The success of the washing was monitored by measuring the protein content at OD 280.

EPO was eluted with buffer H (10 mM Na phosphate, pH 7.0; 80 mM NaCl) at a flow rate of 0.5 ml/min. The elution solution was collected in 1-2 ml factions.

The EPO content of the fractions, wash solutions and the eluate was determined by RP-HPLC by applying an aliquot to a POROS R2/H column.

Fractions of the elution containing EPO (3-6 ml) were pooled. The yield of the hydroxyapatite column was ca. 80 µg EPO (corresponds to ca. 60%). In general the yield of the hydroxyapatite column was between 50 and 65% of the applied butyl-Sepharose pool.

4. Concentration

The pooled EPO fractions from the hydroxyapatite step were concentrated in centrifugation units with an exclusion size of 10 kD (e.g. Microsep from Filtron) to a concentration of 0.1-0.5 mg/ml, 0.01% Tween 20 was added and it was stored in aliquots at −20° C.

Yield Scheme:

|  | EPO (µg) | Yield (%) |
|---|---|---|
| initial | 245 | 100 |
| blue-Sepharose | 175 | 70 |
| butyl-Sepharose column | 130 | 53 |
| hydroxyapatite column | 80 | 33 |
| concentration | 60 | 25 |

The purity of the isolated EPO was about >90%, usually even >95%.

Method 2 in which the butyl-Sepharose step was omitted, was also used to increase the EPO yield. This method can be applied especially to cell culture supernatants without or with addition of 1% (v/v) FCS supplement and yields isolated EPO of approximately the same purity (90-95%). The presence of 5 mM $CaCl_2$ in the equilibration buffer (buffer F) for the hydroxylapatite column led in this method to an improved binding and thus also to an improved reproducible elution behaviour of EPO in the hydroxyapatite step. Therefore method 2 was carried out with the following buffers using in principle the same procedure as method 1:

1. Blue-Sepharose Column:

| | |
|---|---|
| equilibration buffer (buffer A): | 20 mM Tris-HCl, pH 7.0; 5 mM $CaCl_2$; 100 mM NaCl |
| wash buffer 1 (buffer B): | 20 mM Tris-HCl, pH 7.0; 5 mM $CaCl_2$; 250 mM NaCl |
| wash buffer 2 (buffer C): | 20 mM Tris-HCl, pH 7.0 5 mM $CaCl_2$, 250 mM NaCl |
| elution buffer (buffer D): | 100 mM Tris-HCl, pH 7.0 5 mM $CaCl_2$; 2 M NaCl |

2. Hydroxyapatite Column

| | |
|---|---|
| equilibration buffer (buffer F): | 50 mM Tris-HCl, pH 7.0; 5 mM $CaCl_2$; 1 M NaCl |
| wash buffer (buffer G): | 10 mM Tris-HCl, pH 7.0; 5 mM $CaCl_2$; 80 mM NaCl |
| elution buffer (buffer H): | 10 mM Na-phosphate, pH 7.0; 0.5 mM $CaCl_2$; 80 mM NaCl |

Yield Scheme:

|  | EPO (µg) | Yield (%) |
|---|---|---|
| initial | 600 | 100 |
| blue-Sepharose | 450 | 75 |
| hydroxyapatite column | 335 | 55 |
| concentration | 310 | 52 |

The addition of 5 mM $CaCl_2$ to buffers C to G in method 1 also led to an improved binding and more defined elution from the hydroxyapatite column.

Alternatively or additionally the following steps can also be used to purify EPO:
RP-HPLC e.g. with Vydac C4 material
DEAE-Sepharose ff chromatography
diafiltration

EXAMPLE 2

Purification of EPO from Culture Supernatants While Retaining the Isoforms 1-8 (Comparison)

1. Starting Material

EPO from mammalian cells e.g CHO or human cells was fermented by a repeated batch process. A 1000 l fermenter was inoculated with a preculture and the fermenter contents were harvested after ca. 3 to 5 days. After the harvest the cells were removed from the fermentation broth by centrifugation. The cell-free culture supernatant is adjusted to pH 5.0-5.2 with 1 mol/l acetic acid and filtered at 1-9° C.

2. Blue-Sepharose Chromatography

A chromatography column (Amicon P440×500, Amicon, GB) was filled with 60-80 l blue Sepharose and regenerated with 0.5 N NaOH. Subsequently the column was equilibrated with ca. 3 column volumes (CV) acetate buffer.

The cell-free culture supernatant adjusted to pH 5 was absorbed to tie column at a temperature of 10±5° C. and a flow rate of 800-1400 ml/min. The column was re-washed at the same flow rate and 5±4° C. with ca. 1 CV wash buffer 1. This was followed by ca. 2 CV wash buffer 2. Subsequently the column was eluted with ca. 3 CV elution buffer. The total protein peak was collected (ca. 30-60 l) adjusted to pH 6.9 with HCl and stored at 5±4° C. until further processing. The product solution was concentrated in this chromatographic step and a purity of ca. 40-50% was achieved.

| | |
|---|---|
| Equilibration buffer: | 20 mM Na acetate, 5 mM $CaCl_2$, 0.1 M NaCl, pH 5.0 ± 0.2 |
| wash buffer 1: | 20 mM Na acetate, 5 mM $CaCl_2$, 0.25 M NaCl, pH 5.0 ± 0.2 |
| wash buffer 2: | 20 mM Tris-HCl, 5 mM $CaCl_2$, pH 6.5 ± 0.3 |
| elution buffer: | 100 mM Tris-HCl, 5 mM $CaCl_2$, 1 M NaCl, pH 9.0 ± 0.2 |

3. Butyl-Toyopearl Chromatography (Hydrophobic Chromatography)

A chromatography column (Pharmacia BPG 300/500) was filled with 30-40 l butyl-Toyopearl and regenerated with 4 M guanidine-HCl and 0.5 N NaOH. Subsequently the column was equilibrated with at least 3 CV equilibration buffer.

The eluate from the blue-Sepharose column was adjusted to 10% isopropanol and absorbed to the column at a temperature of 27±2° C. and at flow rate of 800-1200 ml/min. The column was re-washed at the same temperature and a flow rate with ca. 1 CV equilibration buffer and then with ca. 2 CV wash buffer. Subsequently it was eluted with ca. 3 CV elution buffer. The total protein peak is collected (ca. 10-18 l), immediately diluted three-fold with dilution buffer and stored at 15° C. until further processing. A purity of ca. 90% was achieved in this chromatography.

| Equilibration buffer: | 20 mM Tris-HCl, 5 mM CaCl$_2$, 0.75 M NaCl, 10% isopropanol, pH 6.9 ± 0.2 |
|---|---|
| wash buffer: | 20 mM Tris-HCl, 5 mM CaCl$_2$, 0.75 M NaCl, 19% isopropanol, pH 6.9 ± 0.2 |
| elution buffer: | 20 mM Tris-HCl, 5 mM CaCl$_2$, 0.75 M NaCl, 27% isopropanol, pH 6.9 ± 0.2 |
| dilution buffer: | 20 mM Tris-HCl, 5 mM CaCl$_2$, pH 6.9 ± 0.2 |

4. Hydroxyapatite Ultrogel Chromatography

A chromatography column (Amicon P440×500 or equivalent) was packed with 30-40 l hydroxyapatite Ultrogel and regenerated with 0.5 N NaOH. Subsequently the column was equilibrated with at least 4 CV equilibration buffer.

The eluate from the butyl-Toyopearl column was absorbed to the column at a temperature of ca. 15° C. and at a flow rate of 500-1200 ml/min. The column was re-washed at the same temperature and a flow rate with ca. 1 CV equilibration buffer and then with ca. 2 CV wash buffer. Subsequently it was eluted with ca. 3 CV elution buffer. The total protein peak was collected (ca. 10-18 l) and stored at 15° C. until further processing. A purity of more than 95% was achieved in this chromatography.

| Equilibration buffer: | 20 mM Tris-HCl, 5 mM CaCl$_2$, 0.25 M NaCl, 9% isopropanol, pH 6.9 ± 0.2 |
|---|---|
| wash buffer: | 10 mM Tris-HCl, 5 mM CaCl$_2$, pH 6.8 ± 0.2 |
| elution buffer: | 10 mM Tris-HCl, 10 mM K phosphate, 0.5 M CaCl$_2$, pH 6.8 ± 0.2 |

5. Reversed Phase HPLC (RP-HPLC)

A preparative HPLC was carried out using a Merck Prepbar 100 separation apparatus (or equivalent) at a temperature of 22±4° C. The separation column (100 mm×400 mm, 3.2 l) was packed with Vydac C4 material. Before use, the column was regenerated by repeatedly applying a gradient of buffer A to 100% solvent and subsequently equilibrated with buffer A.

The eluate from the hydroxyapatite column was acidified with trifluoroacetic acid to ca. pH 2.5 and sterile filtered. Subsequently it was applied to the column at a temperature of 22±4° C. and a flow rate of 250-310 ml/min. The column was eluted at the same temperature and flow rate with a linear gradient of buffer A to buffer B. The elution peak was collected in fractions. The eluate was immediately neutralized by first adding 4 volumes HPLC dilution buffer.

Fractions which have a purity of at least 99% in the analytical HPLC were pooled (pool volume ca. 4-6 l). Trace impurities were separated in this chromatography and a purity of more than 99% was achieved.

| buffer A: | 0.1% trifluoroacetic acid in water |
|---|---|
| buffer B: | 80% acetonitrile, 0.1% trifluoroacetic acid in water |
| HPLC dilution buffer: | 10 mM Na/K phosphate, pH 7.5 ± 0.2 |

6. DEAE-Sepharose ff Chromatography

A chromatography column (Amicon P90×250 or equivalent) was filled with 100-200 ml gel per g applied EPO and regenerated with 0.5 N NaOH. Subsequently the column was equilibrated firstly with 100 mM Na/K phosphate buffer, pH 7.5 and then with at least 12 CV equilibration buffer.

The eluate from the HPLC column was absorbed to the column at a temperature of 5±4° C. and a flow rate of ca. 150 ml/min. The column was rewashed at the same temperature and flow rate with at least 5 CV equilibration buffer and then with ca. 10 CV wash buffer. Subsequently it was again washed with ca. 10 CV equilibration buffer and then eluted with ca. 7 CV elution buffer. The total protein peak was collected (ca. 2-5 l), sterile filtered and dispensed.

In this chromatography the solvent from the HPLC step was separated and trace impurities were removed. The purity is more than 99%.

| equilibration buffer: | 10 mM Na/K phosphate, pH 7.5 ± 0.2 |
|---|---|
| wash puffer: | 30 mM Na-acetate, pH 4.5 ± 0.1 |
| elution buffer: | 10 mM Na/K phosphate, 80 mM NaCl pH 7.5 ± 0.2. |

EXAMPLE 3

Purification of EPO from Culture Supernatants While Retaining the Isoforms 1-4 (Invention)

1. Starting Material

EPO from mammalian cells e.g CHO or human cells was fermented by a repeated batch process. A 10 l fermenter was inoculated with a preculture and the fermenter contents were harvested after ca. 5 days. After the harvest the cells were removed from the fermentation broth by centrifugation. The cell-free culture supernatant was adjusted to pH 5.0-5.2 with 1 mol/l acetic acid and filtered at 1-9° C.

2. Blue-Sepharose Chromatography

A suitable chromatography column was filled with 150-250 ml blue-Sepharose and regenerated with 0.5 N NaOH. Subsequently the column was equilibrated with ca. 3 column volumes (CV) acetate buffer.

The cell-free culture supernatant adjusted to pH 5 was absorbed to the column at a temperature of 10±5° C. and a flow rate of 1-2 CV/h. The column was rewashed at the same flow rate and 5±4° C. with ca. 1 CV wash buffer 1. This was followed by ca. 2 CV wash buffer 2. Subsequently the column was eluted with ca. 3-6 CV elution buffer. The protein peak was collected in fractions. After CE analysis, suitable fractions were pooled, adjusted to pH 6.9 with HCl and stored at 5±4° C. until further processing. The product solution was concentrated in this chromatographic step and impurities and basic isoforms were separated.

| Equilibration buffer: | 20 mM Na-acetate, 5 mM CaCl$_2$, 0.1 M NaCl, pH 5.0 ± 0.2 |
|---|---|
| wash buffer 1: | 20 mM Na-acetate, 5 mM CaCl$_2$, 0.25 M NaCl, pH 5.0 ± 0.2 |
| wash buffer 2: | 20 mM Tris-HCl, 5 mM CaCl$_2$, pH 6.5 ± 0.3 |
| elution buffer: | 50 mM Tris-HCl, 5 mM CaCl$_2$, 0.25 M NaCl, pH 8.0 ± 0.2 |

3. Butyl-Toyopearl Chromatography (Hydrophobic Chromatography)

A suitable chromatography column was filled with 200-300 ml butyl-Toyopearl and regenerated with 4 M guanidine-HCl and 0.5 N NaOH. Subsequently the column was equilibrated with at least 3 CV equilibration buffer.

The eluate from the blue-Sepharose column was adjusted to 10% isopropanol and absorbed to the column at a temperature of 27±2° C. and flow rate of 1-2 CV/h. The column was rewashed at the same temperature and flow rate with ca. 1 CV equilibration buffer and then with ca. 2 CV wash buffer. Subsequently it was eluted with ca. 5-10 CV elution buffer. Fractions were collected from the protein peak and immediately diluted three-fold with dilution buffer. After CE analysis, suitable fractions were pooled and stored at 15° C. until further processing. In this chromatography further basic isoforms were removed and a purity of ca. >80% was achieved.

| | |
|---|---|
| Equilibration buffer: | 20 mM Tris-HCl, 5 mM CaCl$_2$, 0.2 M NaCl, 10% isopropanol, pH 6.9 ± 0.2 |
| wash buffer: | 20 mM Tris-HCl, 5 mM CaCl$_2$, 0.2 M NaCl, 17% isopropanol, pH 6.9 ± 0.2 |
| elution buffer: | 20 mM Tris-HCl, 5 mM CaCl$_2$, 0.2 M NaCl, 23% isopropanol, pH 6.9 ± 0.2 |
| dilution buffer: | 20 mM Tris-HCl, 5 mM CaCl$_2$, pH 6.9 ± 0.2 |

4. Hydroxyapatite Ultrogel Chromatography

A suitable chromatography column was filled with 150-200 ml hydroxyapatite Ultrogel and regenerated with 0.5 N NaOH. Subsequently the column was equilibrated with at least 4 CV equilibration buffer.

The eluate from the butyl-Toyopearl column was absorbed to the column at a temperature of ca. 15° C. and a flow rate of 1-2 CV/h. The column was re-washed at the same temperature and flow rate with ca. 1 CV equilibration buffer and then with ca. 2 CV wash buffer. Subsequently it was eluted with ca. 3 CV elution buffer. The total protein peak was collected and stored at 15° C. until further processing. A purity of mare than 95% was achieved in this chromatography.

| | |
|---|---|
| Equilibration buffer: | 20 mM Tris-HCl, 5 mM Cacl$_2$, 0.06 M NaCl, 7.5% isopropanol, pH 6.9 ± 0.2 |
| wash buffer: | 10 mM Tris-HCl, 5 mM CaCl$_2$, pH 6.8 ± 0.2 |
| elution buffer: | 10 mM Tris-HCl, 10 mM K-phosphate, 0.5 mM CaCl$_2$, pH 6.8 ± 0.2. |

5. Reversed Phase HPLC (RP-HPLC)

A semi-preparative HPLC was carried out using a Vydac C4 separation column (20 mm×250 mm, ca. 80 ml) at a temperature of 22±4° C. Before use the column was regenerated by repeatedly applying a gradient of buffer A to 100% solvent and subsequently equilibrated with buffer A.

The eluate from the hydroxyapatite column was applied to the column at a temperature of 22±4° C. and a flow rate of 8-15 ml/min. The column was eluted at the same temperature and flow rate with a linear gradient of buffer A to buffer B according to the following HPLC protocol. The elution peak was collected in fractions. The eluate was immediately diluted by first adding 4 volumes HPLC dilution buffer.

HPLC protocol:

| Time (min) | Step | % buffer A (v/v) | % buffer B (v/v) |
|---|---|---|---|
| 0.0 | start | 100 | 0 |
| 10.0 | wash 1 | 100 | 0 |
| 20.0 | wash 2 | 50 | 50 |
| 160.0 | wash 3 and elution (*) | 0 | 100 |
| 170.0 | re-wash | 0 | 100 |
| 171.0 | set back to initial conditions | 100 | 0 |

(*) wash 3 and elution conditions: gradient of 50% buffer B to 100% buffer B in 50 to 200 min, preferably 140 min.

Fractions which have a purity of at least 99% in the analytical HPLC and are suitable according to CE analysis were pooled. Trace impurities and residues of basic isoforms were removed in this chromatography and a purity of more than 99% was achieved.

| | |
|---|---|
| buffer A: | 10 mM Na/K phosphate, pH 7.0 ± 0.2 |
| buffer B: | 10 mM Na/K phosphate, 80% acetonitrile, pH 7.0 |
| HPLC dilution buffer: | 10 mM Na/K phosphate, 100 mM NaCl, pH 7.5 ± 0.2 |

6. Diafiltration

A diafiltration apparatus of a suitable size was fitted with a 10 kD cassette and regenerated with 1 N NaOH. Subsequently the apparatus was rinsed free of lye using bulk buffer.

The eluate of the HPLC column was concentrated at a temperature of 5±4° C. and diafiltrated against 10 volumes bulk buffer. The final concentration should be between 1 and 3 mg/ml.

This step serves to remove solvent residues from the HPLC step, to adjust the required bulk buffer conditions and product concentration of the bulk active substance.

| | |
|---|---|
| bulk buffer: | 10 mM Na/K phosphate, 100 mM NaCl, pH 7.5 ± 0.2 |

EXAMPLE 4

Determination of the Specific Activity of EPO in vivo (Bioassay on a Normocythaemic Mouse)

The dose-dependent activity of EPO on the multiplication and differentiation of erythrocyte precursor cells was determined in vivo in mice by means of the increase in reticulocytes in the blood after EPO administration.

For this various doses of the EPO sample to be analysed and of an EPO standard (standardized with the EPO WHO standard) were each administered paranterally to 8 mice. The mice were subsequently kept under constant defined conditions. Blood was collected from the mice 4 days after EPO administration and the reticulocytes were stained with acridine-orange. The recitulocyte count per 30,000 erythrocytes was determined by microfluorimetry in a flow cytometer by analysing the red-fluorescence histogram.

The biological activity was calculated from the values for the reticulocyte counts of the sample and of the standard at different doses according to the method described by Linder of pairwise determination of concentration with parallel straight lines (Linder, "Planen und Auswerten von Versuchen", 3rd. edition, 1969, Birkenhäuser Verlag, Basel).

The EPO preparations CHO 1, CHO 2 and CHO 3 were obtained by purifying EPO from the culture supernatants of CHO cells cultured in serum-free medium which had biological activities of 248,000 (CHO 1), 225,000 (CHO 2) and 186,000 IU/mg (CHO 3) respectively. In four preparations in which EPO was purified from the culture supernatants of human cells, products with specific activities of 220,000 (HeLa 1), 198,000 (HeLa 2), 204,000 (HeLa 3), 176,000 (HeLa 4) and 100,000 IU/mg (HeLa 5) were obtained. The correlation of the values for biological activity with parameters for the sugar structure is given in example 11.

EXAMPLE 5

Determination of the Content of Sialic Acid Residues

The sialic acid content was determined chromatographically by means of HPAEC-PAD (high pH anion exchange chromatography with pulsed amperometric detection) on a Dionex system after enzymatic cleavage of the sialic acids with neuraminidase from *Arthrobacter ureafaciens* (*A. ureaf.*, Boehringer Mannheim).

Preparations each containing 22 µg EPO from various preparations of CHO and human cell lines (e.g. HeLa S3) were adjusted to an EPO concentration of 0.2 mg/ml in 5 mM Na phosphate buffer, pH 7.2. Half of each preparation was used to exactly determine the EPO amount by means of RP-HPLC. 5 mM U neuraminidase from *A. ureaf.* was added to the second half of the preparations and incubated overnight (ca. 18 h) at 37° C. Subsequently the digestion mixtures were halved, diluted 20-fold to 500 µl with $H_2O$ and 50 µl thereof (corresponds to ca. 27 pmol EPO) was applied to the Dionex system. The following chromatographic parameters were used for this:

| column: | CarboPac PA 100 | |
|---|---|---|
| flow: | 1.0 ml/min | |
| detector sensitivity: | 300 nA | |
| gradient: | t (min) | % buffer B |
| | 0 | 17 |
| | 7 | 17 |
| | 9 | 100 |
| | 12 | 100 |
| | 13 | 0 |
| | 20 | 0 |
| buffer A: | 0.1 M NaOH | |
| buffer B: | 0.1 M NaOH; 0.5 M Na acetate | |

The amount of sialic acids in the applied sample was determined with the acid of a calibration line which was obtained from values of a sialic acid standard that was also analysed (Boehringer Mannheim). The sialic acid content (mole sialic acid/mole EPO) was calculated from the result of the sialic acid determination (Dionex system) and the determination of the amount of EPO used by means of RP-HPLC.

The EPO from CHO cells had an average content of 12.9 mole (CHO 1), 11.8 (CHO 2) and 11.7 mole (CHO 3) sialic acid per mole EPO. The EPO preparations derived from human cells had an amount of 13.1 mole (HeLa 1), 13.2 mole (HeLa 2), 13.3 mole (HeLa 3), 11.6 mole (HeLa 4) and 10.8 mole (HeLa 5) sialic acid per mole EPO (cf. also example 11).

EXAMPLE 6

Determination of the Proportions of Biantennary, Triantennary and Tetraantennary Carbohydrate Structures The N-linked carbohydrate structures were analysed chromatographically by HPAEC-PAD on a Dionex system. The asialo oligosaccharides of EPO preparations from CHO and human cell lines (e.g. HeLa S3) were isolated by enzymatic cleavage with N-glycosidase F (Boehringer Mannheim) and neuraminidase from *A. ureaf.* (Boehringer Mannheim).

10 or 30 µg EPO per mixture was desalted by means of MicroCon ultracentrifugation units (Amicon, exclusion size 10 kD) and adjusted with 10 mM Na phosphate buffer, pH 7.2 to a concentration of 0.2 or 0.3 mg/ml. Subsequently 1 U N-glycosidase F and 10 mU neuraminidase was added to each mixture and incubated overnight (ca. 18 h) at 37° C. In order to separate the EPO polypeptide moiety from the cleaved oligosaccharides, the mixtures were centrifuged through Ultrafree centrifugation units (Millipore, exclusion size 10 kD) after incubation and the Ultrafree device was washed again twice with 20 µl $H_2O$. The oligosaccharides contained in the filtrate were made up to 150 µl with $H_2O$ and 100 µl thereof was analysed on the Dionex system. The following chromatographic parameters were used for this:

| column: | CarboPac PA 100 | |
|---|---|---|
| flow: | 1.0 ml/min | |
| detector sensitivity: | 300 nA | |
| gradient: | t (min) | % buffer B |
| | 0 | 0 |
| | 2 | 0 |
| | 60 | 10 |
| | 62 | 100 |
| | 67 | 100 |
| | 69 | 0 |
| | 80 | 0 |
| buffer A: | 0.1 M NaOH | |
| buffer B: | 0.1 M NaOH; 0.5 M Na acetate | |

The peaks were identified in a chromatogram of N-sugars of the complex type by standard oligosaccharides (Oxford Glyco Systems) and verified by enzymatic digestion of the oligosaccharides of EPO with the enzyme endo-β-galactosidase or fucosidase and subsequent analysis on the Dionex system. The percentages of biantennary, triantennary and tetraantennary structures were calculated by means of the areas of the peaks that represent the corresponding N-sugar structure relative to the total peak area (sum of the peak areas of biantennary, triantennary and tetraantennary structures).

The EPO derived from CHO cells had a content of 4.2% biantennary carbohydrate structures, 22.3% triantennary carbohydrate structures and 73.5% tetraantennary carbohydrate structures (CHO3) and a content of 86.7% tetraantennary carbohydrate structures in the CHO 1 preparation and 78.6% in CHO 2. The contents of biantennary/triantennary/tetraantennary structures in the preparations of EPO from human cell lines were 5.8/8.8/85.4% for HeLa 1, 5.1/12.7/82.2% for HeLa 2, 4.1/17.7/78.2% for HeLa 3, 10.1/19.2/70.6% for HeLa 4 and 12.6/25.4/62% for HeLa 5 (cf. also example 11).

EXAMPLE 7

Determination of the Average Content of N-acetyl-lactosamine Units and the Average Content of Additional N-acetyl-lactosamine Units (Repeats)

The total number of N-acetyl-lactosamine units in the N-linked carbohydrate structures of EPO (i.e. in the core carbohydrate structures plus repeats) was calculated from the peak areas of the chromatograms of the experiments of example 6.

The number of the average content (n) of N-acetyl-lactosamine units per carbohydrate chain was calculated as follows:

$$n = \Sigma \, \% \, (bi) \times 2 + \% \, (tri) \times 3 + \% \, (tetra) \times 4 + \% \, (tri + 1r) \times 4 + \% \, (tetra + 1r) \times 5 + \% \, (tri + 2r) \times 5 + \% \, (tetra + 2r) \times 6$$

in which
% (bi) percentage of biantennary structures relative to the total amount (100%) of N-linked carbohydrate structures
% (tri)=percentage of tetraantennary structures without additional N-acetyl-lactosamine units
% (tetra)=percentage of tetraantennary structures without additional N-acetyl-lactosamine units
% (tri+1r)=percentage of triantennary structures with 1 additional N-acetyl-lactosamine unit
% (tetra+1r)=percentage tetraantennary structures with 1 additional N-acetyl-lactosamine unit
% (tri+2r)=percentage of triantennary structures with 2 additional N-acetyl-lactosamine units
% (tetra+2r)=percentage of tetraantennary structures with 2 additional N-acetyl-lactosamine units In the case of EPO from CHO cells an average number of 4.3 (CHO 1), 4.4 (CHO 2) and 4.2 (CHO 3) N-acetyl-lactosamine units per carbohydrate chain was found. In the EPO preparations from human cells a number of N-acetyl-lactosamine units of 4.0 (HeLa 1), 4.0 (HeLa 2), 3.9 (HeLa 3), 3.75 (HeLa 4) and 3.6 (HeLa 5) was found (cf also example 11).

Due to the fact that EPO contains 3 N-linked sugar structures, the total number of N-acetyl-lactosamine units is threefold higher. With reference to the total glycosylation of EPO the number of N-acetyl-lactosamine units in the EPO from CHO cells is therefore 12.9 (CHO 1), 13.2 (CHO 2) and 12.6 (CHO 3). In the EPO preparations of human cells the corresponding values were 12.0 (HeLa 1), 11.9 (HeLa 2), 11.7 (HeLa 3), 11.25 (HeLa 4) and 10.8 (HeLa 5).

The product of the number of N-acetyl-lactosamine units per carbohydrate structure multiplied by the respective sialic acid content yielded values of 55.5 (CHO 1), 52 (CHO 2) and 49.3 (CHO 3) for EPO from CHO cells. In the case of EPO preparations from human cells the corresponding values were 52.4 (HeLa 1), 52.5 (HeLa 2), 51.3 (HeLa 3), 43.5 (HeLa 4) and 38.9 (HeLa 5).

With reference to the total glycosylation of EPO (3 N-linked carbohydrate structures) the product of the number of N-acetyl-lactosamine units multiplied by the respective sialic acid content is for EPO from CHO cells 166.5 (CHO 1), 156 (CHO 2) and 147.9 (CHO 3) respectively. In the EPO preparations from human cells the corresponding values were 157.2 (HeLa 1), 157.5 (HeLa 2), 153.9 (HeLa 3)., 130.5 (HeLa 4) and 116.7 (HeLa 5) cf also example 11.

A further important parameter is the amount of N-acetyl-lactosamine units which can be bound to the core carbohydrate structures as so-called repeats (cf. e.g. FIG. 1) The repeat content is specified as the percentage of repeat-containing carbohydrate structures relative to the sum of all N-linked carbohydrate structures (bi+tri+tetra=100%).

This proportion of repeats can be different in EPO preparations from CHO cells and from human cells. Thus repeat percentages of 39.6% (CHO 1), 51% (CHO 2) and 36.8% (CHO 3) were determined for the preparations from CHO cells. Repeat percentages of 18% (HeLa 1), 16.5% (HeLa 2), 14.0% (HeLa 3), 12.2% (HeLa 4) and 9.8% (HeLa 5) were determined for the preparations from human cells (cf. example 11).

EXAMPLE 8

Influencing the Biological Activity of EPO by Controlled and Feeding According to Requirements Cultures were carried out as repeated batch processes with feeding as required (repeated fed batch) at a temperature of 36.5° C. For this serum-free, protein-poor culture medium was placed in a stirred fermenter (total working volume: 10 L) and inoculated once with an inoculum culture. The cell density after inoculation was in the range of $3 \pm 1 \times 10^5$ living cells/ml. After a growth phase of 144±24 hours, a portion of the culture broth was harvested. The remainder of the culture broth remained in the fermenter and represented the inoculum for the next growth phase; for this purpose the fermenter was again filled up with fresh medium to the working volume.

The culture supernatant containing EPO was obtained by centrifuging the fermentation culture.

Nutrient solution was continuously supplied to the culture during the growth phase. For this purpose a storage vessel containing nutrient solution was coupled to the fermenter. The nutrient solution contained amino acids, vitamins, insulin, trace elements, salts, glutamine and carbohydrates. Two fermentations were carried out as follows:

In fermentation A the nutrient solution contained D-(+)-glucose as the sugar and in fermentation B the sugars were D-(+)-glucose, D-(+)-galactose and D-(+)-mannose. The mass ratio of glutamine to the sugars was 1:2.2:3.6:6 in fermentation B. The concentration of the individual sugars in the nutrient solution was between 7.2 and 18 g/l.

The glutamine concentration in the culture was periodically analysed in fermentation B and the consumption was calculated. The momentary volume flow of the nutrient solution was matched to the requirement of the cells for nutrients. In fermentation A the glutamine concentration was not used as a controlled variable. The nutrient solution in fermentation B contained a mixture of the sugars D-(+)glucose, D-(+) galactose and D-(+)mannose in a mass ratio of 2:3:5. The concentration of all sugars in the fermenter was kept in the range 2 to 6 g/l during the culture by corresponding feeding. The cell density changed during the growth to more than $20 \times 10^5$ cells/ml, typically $30 \pm 10 \times 10^5$ cells/ml up to the time of harvest. At the time of harvest the concentration of EPO was typically 40±10 mg/l.

The concentration of human erythropoietin was determined, for example by ELISA, in the harvested culture broths. A percentage distribution of the isoforms of this protein that occurred was for example determined by separating with capillary zone electrophoresis (CZE).

Table 1 shows a comparison of the distribution of EPO isoforms between a fermentation A fed with a nutrient solution containing glucose and a fermentation B fed with a nutrient solution containing glucose, mannose and galactose in a controlled and requirement-oriented manner. The contents of EPO isoforms in fermentation B were calculated as percentages of the corresponding isoforms of fermentation A. The latter were each standardized to 100%. The data show that the desired higher glycosylated EPO isoforms 2-4 are present in a substantially higher proportion during fermentation compared with fermentation A.

TABLE 1

| | Isoform name in the CZE | | | | | | | |
|---|---|---|---|---|---|---|---|---|
| | 1 [%] | 2 [%] | 3 [%] | 4 [%] | 5 [%] | 6 [%] | 7 [%] | 8 [%] |
| Fermentation A: feeding with glucose | n.d. | 100 | 100 | 100 | 100 | 100 | 100 | 100 |
| Fermentation B: feeding with glucose, mannose and galactose as required | n.d. | 136 | 140 | 115 | 102 | 91 | 76 | 55 | n.d. = not determinable, since the value is below the detection limit

The isoform pattern obtained with feeding was reproducible in four successive harvests from a fermentation with controlled and demand-oriented feeding of the nutrient solution.

EXAMPLE 9

Influencing the Biological Activity of EPO by Changing the Culture Temperature The procedure was as described in example 8 (fermentation B) in a fed-splitbatch process with controlled and demand-oriented feeding except that the fermenter temperature was 35.0° C. instead of 36.5° C. and the fermentation was carried out on a 1000 l scale.

Table 2 shows a comparison of the EPO isoform distribution between a fermentation C at 36.5° C. and a fermentation D at 35.0° C. each with controlled feeding of a nutrient solution. The contents of EPO isoforms in fermentation D were calculated as percentages of the corresponding isoforms of fermentation C. The latter were each standardized to 100%. The data show that the acidic EPO isoforms 2 to 4 can be considerably increased by decreasing the temperature.

TABLE 2

| | Isoform name in the CZE | | | | | | | |
|---|---|---|---|---|---|---|---|---|
| | 1 | 2 | 3 | 4 | 5 | 6 | 7 | 8 |
| | Relative isoform distribution | | | | | | | |
| | [%] | [%] | [%] | [%] | [%] | [%] | [%] | [%] |
| Fermentation C: temperature 36.5° C. | n.d. | 100 | 100 | 100 | 100 | 100 | 100 | 100 |
| Fermentation D: temperature 35.0° C. | n.d. | 131 | 116 | 110 | 94 | 100 | 88 | 86 | n.d. = not determinable, since the value is below the detection limit

EXAMPLE 10

Influencing the Biological Activity of EPO by Changing the Carbohydrate Composition in the Medium The process presented in the following shows that it is possible to change the quality of human erythropoietin by changing the carbohydrate supply in the feeding medium.

Two variants of the process described above are shown (called fermentation E and fermentation F in the following) which differ in the composition of the media used.

In both preparations the formulation of the culture medium is based on modified eRDF medium. No serum was used but rather recombinant insulin (only protein additive) and further supplements (e.g. selenite, putrescine, hydrocortisone, iron sulfate) which are usually used in serum-free or protein-free media.

The feed nutrient solution is also based on modified eRDF medium but does not contain the salts KCl, $Na_2HPO_4$ and NaCl.

The major difference between fermentation E and F is the addition of various monosaccharides to the feed medium.

Fermentation E:

The usual sugar D-(+)-glucose was used for fermentation E. The initial concentration was 3 g/l. By appropriately feeding the glucose-containing nutrient solution, the glucose concentration in the culture broth was maintained at 3±0.5 g/l during the entire culture.

The culture period was typically 100±20 h. The concentration of EPO was typically 40±10 mg/l at the time of harvest.

Fermentation F:

In addition to D-(+)-glucose, the sugars D-(+)-galactose and D-(+)-mannose were added in a mass ratio of ca. 1:2:3 to the feed medium for fermentation F. During the culture the concentration of all sugars was kept in a range between 0.25 g/l and 3.5 g/l by appropriate feeding.

The culture period for this growth was typically 100±20 hours. The concentration of EPO at the time of harvest was typically 40±10 mg/l.

Erythropoietin was purified from the culture supernatants. The purification procedure was designed (cf. example 2) such that the distribution of relevant isoforms of the glycoprotein was not influenced.

The isoform distribution of the purified erythropoietin was determined as described above.

The carbohydrate structures of the isoforms of human erythropoietin and their distribution in the harvested culture supernatants was different in fermentation E and fermentation F. Fermentation E has a considerable higher proportion of isoforms 2, 3 and 4 compared to fermentation F. These differences are caused by feeding the monosaccharides mannose and galactose (cf. FIG. 2).

The biological activity determined by the normo mouse test (example 4) correlates with the distribution and the carbohydrate structures of the EPO isoforms (FIG. 3). The carbohydrate structures of the EPO preparations obtained from the culture supernatants E and F were examined with CZE and HPAEC analysis.

The antennarity (content of bistructures, tristructures and tetrastructures), the content of N-acetyl-lactosamine units (LE), the sialic acid content (SA) and the product of LE and SA of the two EPO preparations are shown in Table 3.

TABLE 3

|  | bi. [%] | tri [%] | tetra [%] | SA content | LE content | LE × SA |
|---|---|---|---|---|---|---|
| Fermentation E | 12.6 | 25.4 | 62.0 | 10.8 | 10.8 | 116.7 |
| Fermentation F | 10.1 | 19.2 | 70.6 | 11.6 | 11.25 | 130.5 |

EXAMPLE 11

Correlation of the Specific Activity and Carbohydrate Structures

In this example investigations on the dependency of the biological activity of individual EPO isoforms on the carbohydrate structures are summarized. For this isoforms (IF) from various EPO sources (different batches of EPO from CHO cells and human cells) were isolated and compared.

11.1 Isolation of Individual Isoforms of EPO by Means of Isoelectric Focussing (IEF) and Western Blot A). Procedure for IEF Gel Electrophoresis and Electro-blotting on Nitrocellulose In order to isolate individual isoforms in a pure form, an EPO solution composed of a mixture of several isoforms was desalted in ultrafree centrifugation units and concentrated (5-10 mg/ml). 350-1000 µg of this solution was applied to an IEF polyacrylamide ready-made gel from Serva (Servalyt Precotes, pH 3-5, 300 µm, 125×125 mm) (in 5-10 lanes containing 70-100 µg EPO per lane). The IEF was carried out at 2500 V for 3.5 h at 5° C.; subsequently the gel was blotted on nitrocellulose (wet blot in Tris/glycine buffer containing methanol but without SDS for 3 h at 200 mA). After the blotting process, the gel was removed and the nitrocellulose membrane was stained with Ponceau S. The stained isoforms were cut out and again completely destained with $H_2O$ or TBS buffer (100 mM Tris, pH 7.4; 150 mM NaCl).

B) Extraction of the Isoforms from the Membrane

The destained nitrocellulose strips containing the respective isoforms were placed in 2 ml Eppendorf vessels (corresponding to 3-4 lanes of the IEF gel), 1.5 ml acetone was added and the nitrocellulose was dissolved by vortexing. It was incubated overnight at −20° C. to optimally precipitate the EPO. Subsequently the precipitate containing EPO was isolated for 10 min in a bench centrifuge at 14,000 rpm. The precipitate was washed 2-3 times with 1 ml acetone and then dried at room temperature or 37° C. under a stream of nitrogen. The EPO precipitate was subsequently dissolved in 20 mM Na-phosphate buffer, pH 7.2 containing 0.01% Tween 20 and stored at −20° C. until further analysis.

C) Isolation of Isoforms from Prefractionated EPO Solutions

Individual isoforms were isolated as described in A) and B) with the qualification that the initial EPO solutions contained 7-8 instead of only 3-4 isoforms. The starting material was EPO fractions which had been isolated by a DE chromatography (anion exchanger). These fractions contained only 3-4 isoforms (e.g. isoform 6-8 or isoform 1-4). In order to isolate the isoform packages, a suitable chromatography column was filled with 1-2 ml DEAE-Sepharose ff per 10 mg applied EPO and regenerated with 0.5 M NaOH. Subsequently the column was firstly equilibrated with 2 CV neutralization buffer and then with at least 5 CV equilibration buffer.

A purified EPO preparation comprising 8 isoforms was absorbed at a temperature of 5±4° C. and a flow rate of up to 15 CV/h. The column was then washed with 2 to 3 CV equilibration buffer and subsequently rinsed with wash buffer until the pH value was 5.0 (ca. 5 CV).

Various isoform packages were eluted by increasing the NaCl concentration in the elution buffer in 10 mM steps beginning at 20 mM NaCl. The basic isoforms bind weakly to the ion exchanger and elute correspondingly at low ionic strengths, the acidic isoforms elute at higher NaCl concentrations up to 70 mM NaCl. The amount of the isoforms eluted at a certain NaCl concentration depends strongly on the starting material and the elution volume. As a rule elution was continued at the individual steps until the OD 280 had decreased to about 50% of the maximum value at this NaCl concentration. This corresponded to between 15 and 40 CV. Additional fractionation of the eluted isoform packages within an NaCl concentration resulted in a further separation of the isoforms. The travel rate of the column was up to 15 CV/h.

| Neutralisation buffer: | 100 mM Na/K phosphate, pH 7.5 ± 0.2 |
|---|---|
| Equilibration buffer: | 10 mM Na/K phosphate, pH 7.5 ± 0.2 |
| Wash buffer: | 30 mM NaAc/HAc, pH 5.0 ± 0.2 |
| Elution buffer: | 10 mM NaAc/HAc, pH 5.0 ± 0.2, 20 mM NaCl, or concentration increased in 10 mM steps to 70 mM NaCl |

Individual pure isoforms were isolated from the isoform packages obtained in this manner by purification as described in A) and B).

The pure isoforms (IF) obtained from A-C were numbered in accordance with their isoelectric point (pI) from acidic to basic. Isoform 2 (IF2) is the most strongly acidic isolated isoform with the lowest pI. Isoform 8 is the most strongly basic with the highest pI. Isoform 2 was the isoform with the lowest pI which could be isolated in adequate amounts from the starting mixture. Only 1-2% of isoform 1 was present in the starting mixture so that it was not possible to obtain adequate amounts for a complete analysis.

The following analyses were carried out to characterize pure isoforms:

determination of the amount and yield by means of RP-HPLC determination of the purity and identity by capillary electrophoresis and isoelectric focussing.

The yield of individual isoforms was generally between 20% and 30% of the isoform used in the starting mixture.

The purity of the isoforms was usually >90%, mostly even >94%.

11.2 Results

The following data were obtained for the purified isoforms (IF):

relative distribution of the N-linked carbohydrate structures (proportion of biantennary, triantennary and tetraantennary structures relative to the total glycosylation) and the repeat content biological activity in the normo mouse test sialic acid content These determinations were essentially carried out by the previously described methods.

The sialic acid content of isolated isoforms was not determined separately for each individual isoform preparation but was carried out on 1-3 preparations as an example for each of the isoforms 2-8 of EPO from CHO cells or isoforms 2-6 of EPO from human cells.

The rounded, whole number sialic acid values of each isoform were used to calculate the product of the content of N-acetyl-lactosamine units (LE value) and the sialic acid content (SA).

These rounded SA values were as follows for EPO from CHO cells and human cells: 14 (IF2), 13 (IF3), 12 (IF4), 11 (IF5), 10 (IF6), 9 (IF7) and 8 (IF8).

Table 4 contains data on the correlation between the specific activity and carbohydrate structures of various EPO preparations from CHO cells (CHO 1, CHO 2 and CHO 3) as well as from human cells (HeLa 1 to 5). The table shows the correlation between the biological activity and the average total number of N-acetyl-lactosamine units (LE) in the EPO molecule, the average sialic acid content (SA) as well as the product LE×SA.

Table 5 contains data on the correlation between the biological activity and the average total number of N-acetyl-lactosamine units (LE) in the EPO molecule, the average sialic acid content (SA) as well as the product LE×SA of isolated isoforms of a non pre-fractionated EPO batch from CHO cells.

Table 6 contains a comparison of various preparations (A and B) of an isoform (IF2 or IF5) which was isolated from various fractions of a prefractioned EPO batch from CHO cells i.e. 2 preparations (A and B) of the isoforms 2 and 5 were analysed in each case. The prefractionation was carried out by means of a DE anion exchanger as described in example 11.1C. The two preparations A and B of the isoforms IF2 and IF5 were isolated from different fractions of the DE column (IF2 from fractions 5 and 6 and IF5 from fractions 2 and 3). Fraction 5 or 2 from which IF2/A or IF5/A respectively was isolated, eluted earlier (at a lower salt concentration) from the DE-Sepharose column than fractions 6 or 3 from which IF2/B or IF5/B respectively were isolated. However, preparations A and B of isoforms 2 or 5 respectively did not differ in their properties in the subsequent isoelectric focussing or in the capillary electrophoresis i.e. both preparations of IF2 or IF5 have the same sialic acid content. However, it was surprisingly found that the isoforms from preparation A have a significantly higher biological activity than the corresponding isoforms from preparation B due to their higher LE value and the higher content of repeat structures. The dependency described in Table 6 of the biological activity of the isoform on the total number of N-acetyl-lactosamine units contained in the EPO molecule at the same sialic acid content was not only observed for isoforms 2 and 5 but also for other isoforms.

Table 7 compares corresponding isoforms from various EPO sources (CHO cells or human HeLa S3 cells). Also in this case a correlation was found between the biological activity and the LE×SA value.

Hence in all tables a correlation can be seen between the product of the number of N-acetyl-lactosamine units (LE) and the sialic acid content (SA) and the biological activity. A high value of the product LE×SA is always associated with a high biological activity.

TABLE 4

| Name | tetra ant. (in %) | repeat[1] (in %) | LE | SA mole/ mole | LE × SA | Specific activity KU/mg |
|---|---|---|---|---|---|---|
| CHO 1 | 86.7 | 39.6 | 12.9 | 12.9 | 166.4 | 248 |
| CHO 2 | 78.6 | 51 | 13.2 | 11.8 | 155.8 | 225 |

TABLE 4-continued

| Name | tetra ant. (in %) | repeat[1] (in %) | LE | SA mole/ mole | LE × SA | Specific activity KU/mg |
|---|---|---|---|---|---|---|
| CHO 3 | 73.5 | 42.6 | 12.6 | 11.7 | 147.4 | 186 |
| HeLa 1 | 85.4 | 18.0 | 12.0 | 13.1 | 157.2 | 220 |
| HeLa 2 | 82.2 | 16.5 | 11.9 | 13.2 | 157.1 | 198 |
| HeLa 3 | 78.2 | 14.0 | 11.7 | 13.3 | 155.6 | 204 |
| HeLa 4 | 70.6 | 12.2 | 11.25 | 11.6 | 130.5 | 176 |
| HeLa 5 | 62 | 9.8 | 10.8 | 10.8 | 116.7 | 100 |

LE: N-acetyl-lactosamine units
SA: sialic acid content of the EPO preparation
[1]percentage of all sugar structures with additional LE extensions relative to the total amount of sugar structures (bi + tri + tetra = 100%)

TABLE 5

| | tetra ant. (in %) | repeat[1] (in %) | LE | SA mole/ mole | LE × SA | Specific activity KU/mg |
|---|---|---|---|---|---|---|
| IF2 | 98 | 48 | 13.7 | 14 | 191.1 | 400 |
| IF3 | 86 | 43 | 13.1 | 13 | 170.3 | 280 |
| IF4 | 75 | 40 | 12.6 | 12 | 151.2 | 200 |
| IF5 | 64 | 39 | 12.0 | 11 | 132 | 150 |
| IF6 | 56 | 41 | 11.4 | 10 | 114 | 75 |
| IF7 | 42 | 39 | 11.1 | 9.0 | 100 | 40 |
| IF8 | 34 | 33 | 10.5 | 8.0 | 84 | 19 |

LE: N-acetyl-lactosamine units (calculated as in example 7)
SA: sialic acid content of the respective isoform
[1]percentage of all sugar structures with additional LE extensions relative to the total amount of sugar structures (bi + tri + tetra = 100%)

TABLE 6

| | tetra ant. (in %) | repeat[1] (in %) | LE | SA mole/ mole | LE × SA | Specific activity KU/mg |
|---|---|---|---|---|---|---|
| IF2/A | 99 | 54 | 14.1 | 14 | 197.4 | 396 |
| IF2/B | 97 | 31 | 12.9 | 14 | 180.6 | 330 |
| IF5/A | 64 | 58 | 13.2 | 11 | 145.2 | 206 |
| IF5/B | 55 | 32 | 11.4 | 11 | 125.4 | 112 |

LE: N-acetyl-lactosamine units (calculated as in example 7)
SA: sialic acid content of the respective isoform
[1]percentage of all sugar structures with additional LE extensions relative to the total amount of sugar structures (bi + tri + tetra = 100%)

TABLE 7

| | tetra ant. (in %) | repeat[1] (in %) | LE | SA mole/ mole | LE × SA | Specific activity KU/mg |
|---|---|---|---|---|---|---|
| IF2 (CHO 2) | 99 | 58 | 14.4 | 14 | 201.6 | 440 |
| IF2 (CHO 3) | 98 | 48 | 13.7 | 14 | 191.8 | 400 |
| IF2 (HeLaS3) | 99 | 24 | 12.9 | 14 | 118.8 | 240 |
| IF5 (CHO 2) | 68 | 48 | 12.9 | 11 | 141.9 | 175 |
| IF5 (CHO 3) | 64 | 39 | 12.0 | 11 | 132.0 | 150 |
| IF5 (HeLaS3) | 70 | 15 | 10.8 | 11 | 119.0 | 60 |

LE: N-acetyl-lactosamine units (calculated as in example 7)
SA: sialic acid content of the respective isoform
[1]percentage of all sugar structures with additional LE extensions relative to the total amount of sugar structures (bi + tri + tetra = 100%)

The dependency of the biological activity of EPO on the proportion of N-linked carbohydrate structures with additional N-acetyl-lactosamine units (repeats) is shown in FIG. 4 using individual isoforms as an example. The isoforms were isolated from EPO preparations containing different proportions of repeat-containing carbohydrate structures (EPO 1 with ca. 50%, EPO 2 with ca. 40% and EPO 3 with ca. 15% repeat-containing structures). The biological activity of corresponding isoforms (same content of sialic acids and about the same antennarity) decreases as the proportion of repeat-containing carbohydrate structures decreases in the isoforms. This characteristic can be observed for isoform 2 up to at least isoform 7.

The invention claimed is:

1. A process for manufacturing an erythropoietin (EPO) composition consisting essentially of glycosylated EPO molecules which contain, on average, at least 4.3 N-acetyl-lactosamine units per N-linked carbohydrate chain per EPO molecule in said composition, or an average of at least 13.0 N-acetyl-lactosamine units with reference to total N-glycosylation of an EPO molecule in said composition, comprising culturing a cell capable of producing said glycosylated EPO molecules, under conditions favoring production thereof, said conditions comprising a temperature of 35° C., wherein said composition contains a higher amount of EPO isoforms IF2, IF3, and IF4 than a composition produced by culturing said cells at 36.5° C.

2. A process for manufacturing an erythropoietin (EPO) composition consisting of glycosylated EPO molecules which contain an average number of at least 4.3 N-acetyl-lactosamine units per N-linked carbohydrate chain or on average at least 13.0 N-acetyl-lactosamine units with reference to the total N-glycosylation of an EPO molecule comprising culturing a cell capable of producing said glycosylated EPO molecules, under conditions favoring production thereof, said conditions comprising a temperature of 35° C., wherein said composition contains a higher amount of EPO isoforms IF2, IF3, and IF4 than a composition produced by culturing said cells at 36.5° C.

3. The process of claim 1 or 2, wherein the number of N-acetyl-lactosamine units is at least 4.5 per N-linked carbohydrate chains or at least 13.5 with reference to the total N-glycosylation.

4. A process for manufacturing an erythropoietin (EPO) composition, consisting essentially of glycosylated EPO molecules, wherein (i) the product of the average number of N-acetyl-lactosamine units per N-linked carbohydrate chain and average sialic acid content per molecule of PEO is at least 43.3 of (ii) the product of total N-glycosylation of an EPO molecule in said composition and average sialic acid content per molecule of EPO is at least 130, comprising culturing a cell capable of producing said glycosylated EPO molecules, under conditions favoring production thereof, said conditions comprising a temperature of 35° C., wherein said composition contains a higher amount of EPO isoforms IF2, IF3, and IF4 than a composition produced by culturing said cells at 36.5° C.

5. A process for manufacturing an erythropoietin (EPO) composition, consisting of glycosylated EPO molecules, wherein (i) the average value of the product of average number of N-acetyl-lactosamine units per N-linked carbohydrate chain of an EPO molecule in said composition and average sialic acid content per molecule of EPO is at least 43.3 or (ii) the average value of the product of total N-glycosylation of an EPO molecule in said composition and average sialic acid content per molecule of EPO in said composition is at least 130, comprising culturing a cell capable of producing said glycosylated EPO molecules, under conditions favoring production thereof, said conditions comprising a temperature of 35° C., wherein said composition contains a higher amount of EPO isoforms IF2, IF3, and IF4 than a composition produced by culturing said cells at 36.5° C.

6. The process of claim 4 or 5, wherein (i) is at least 46.7, or (ii) is at least 140.

7. The process of claim 4 or 5, wherein said glycosylated EPO molecules contain, on average, either (i) at least 4.3 N-acetyl-lactosamine units with reference to an N-linked carbohydrate chain of said EPO molecule, or (ii) at least 13.0 N-acetyl lactosamine units per EPO molecule, with reference to the total N-glycosylation of said EPO molecule.

8. The process of claim 1, 2, 4, or 5, wherein said EPO compositions contain from 2 to 5 glycosylated EPO isoforms.

9. The process of claim 8, wherein said EPO compositions contain 3 or 4 glycosylated EPO isoforms.

10. The process of claim 1 or 4, wherein said composition has a specific activity in vivo of at least 175,000 IU/mg of protein.

11. The process of claim 10, wherein said composition has a specific activity in vivo of at least 200,000 IU/mg of protein.

12. The process of claim 1 or 4, wherein the average sialic acid content per molecule of glycosylated EPO is at least 11.

13. The process of claim 1, 2, 4, or 5, wherein said glycosylated EPO molecules are produced by expression of an exogenous nucleic acid molecule in a mammalian cell.

14. The process of claim 13, wherein said mammalian cell is a CHO cell and the proportion of carbohydrate chains with N-acetyl lactosamine extensions (repeats) relative to the total number of N-linked carbohydrate chain is at least 30%.

15. The process of claim 14, wherein the value for the product of (i) the proportion of carbohydrate chains with N-acetyl lactosamine repeats relative to the total number of carbohydrate chains expressed in %, and (ii) the proportion of tetraantennary structures relative to the total number of carbohydrate chains expressed in % is at least 2400.

16. The process of claim 1, 2, 4 or 5, wherein said glycosylated EPO molecules are produced by expression of an endogenous nucleic acid molecule in a human cell.

17. The process of claim 16, wherein the proportion of carbohydrate chains with N-acetyl lactosamine repeats, relative to the total number of carbohydrate chains is at least 10%.

18. The process of claim 17, wherein the value for the product of (i) the proportion of carbohydrate chains with N-acetyl lactosamine repeats relative to the total number of carbohydrate chains expressed in %, and (ii) the proportion of tetraantennary structures relative to the total number of carbohydrate chains expressed in % is at least 800.

19. The process of claim 13, wherein said mammalian cell is cultured in a serum-free medium.

20. The process of claim 16, wherein said human cell is cultured in a serum-free medium.

21. The process of claim 1, 2, 4 or 5, further comprising a diluent, an auxiliary substance or a carrier.

22. The process of in any of claim 1, 2, 4, or 5, further comprising separating said glycosylated EPO molecules from other components of an EPO composition.

23. The process of claim 1, 2, 4 or 5, further comprising adding at least two carbohydrates to a culture medium in which said cell is cultured.

24. The process of claim 1, 2, 4 or 5, further comprising adding at least three carbohydrates to a culture medium in which said cell is cultured.

25. The process of claim 23, wherein said carbohydrates comprise glucose, mannose, or galactose.

26. The process of claim 24, wherein said carbohydrates comprise glucose, mannose and galactose.

27. The process of claim 1, 2, 4 or 5, further comprising the controlled addition of at least one of (i) an essential amino acid, and (ii) a carbohydrate, to a culture medium containing said cell.

28. The process of claim 27, further comprising determining the concentration of glutamine in the culture medium in which said cell is cultured, to determine whether to add said essential amino acid or said carbohydrate.

29. The process of claim 27, comprising adding (i) or (ii) over the entire growth phase of said cell.

30. The process of claim 27, comprising adding at least two carbohydrates.

31. The process of claim 30, comprising adding at least three carbohydrates.

32. The process of claim 1, wherein said temperature is from 33° C. to 35.0° C.

33. The process of claim 22, comprising separating said glycosylated EPO molecules via reverse phase chromatography, at a pH of from 6-8.

34. The process of claim 33, wherein said reverse phase chromatography comprises eluting with acetonitrile, ethanol or isopropanol.

35. The process of claim 22, comprising separating said glycosylated EPO molecules via affinity chromatography with a triazine dye.

36. The process of claim 22, comprising separating said glycosylated EPO molecule via affinity chromatography using a lectin.

* * * * *